(12) United States Patent
Dooly et al.

(10) Patent No.: US 10,531,690 B2
(45) Date of Patent: Jan. 14, 2020

(54) ELECTRONIC SMOKING ARTICLE WITH IMPROVED STORAGE OF AEROSOL PRECURSOR COMPOSITIONS

(71) Applicant: RAI Strategic Holdings, Inc., Winston-Salem, NC (US)

(72) Inventors: Grady Lance Dooly, Winston-Salem, NC (US); Stephen Benson Sears, Siler City, NC (US); Karen V. Williams, Winston-Salem, NC (US); Gary M. Dull, Lewisville, NC (US); Steven L. Worm, Raleigh, NC (US); Wesley Steven Jones, Lexington, NC (US); Steven Lee Alderman, Lewisville, NC (US); Paul A. Brinkley, Winston-Salem, NC (US); Jack Gray Flinchum, Jr., Clemmons, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 0 days.

(21) Appl. No.: 15/964,912

(22) Filed: Apr. 27, 2018

(65) Prior Publication Data
US 2018/0242647 A1    Aug. 30, 2018

Related U.S. Application Data

(62) Division of application No. 14/158,264, filed on Jan. 17, 2014, now Pat. No. 9,974,334.

(51) Int. Cl.
*A24F 47/00*    (2006.01)
*B65B 5/06*    (2006.01)

(52) U.S. Cl.
CPC .............. *A24F 47/008* (2013.01); *B65B 5/06* (2013.01)

(58) Field of Classification Search
CPC .... A24F 47/008; A24F 47/002; A24F 47/004; A24F 47/006; B65B 5/06; A61M 15/06
See application file for complete search history.

(56) References Cited

U.S. PATENT DOCUMENTS

| | | | |
|---|---|---|---|
| 1,771,366 A | 7/1930 | Wyss et al. |
| 2,057,353 A | 10/1936 | Whittemore, Jr. |
| 2,104,266 A | 1/1938 | McCormick |
| 2,805,669 A | 9/1957 | Meriro |
| 3,200,819 A | 8/1965 | Gilbert |
| 3,316,919 A | 5/1967 | Green et al. |

(Continued)

FOREIGN PATENT DOCUMENTS

| | | |
|---|---|---|
| AU | 276250 | 7/1965 |
| CA | 2 641 869 | 5/2010 |

(Continued)

*Primary Examiner* — Joseph S Del Sole
*Assistant Examiner* — Mohamed K Ahmed Ali
(74) *Attorney, Agent, or Firm* — Womble Bond Dickinson (US) LLP

(57) ABSTRACT

The present disclosure relates to electronic smoking articles exhibiting improved moisture control of a reservoir contained therein. The reservoir can be formed of fibrous materials, such as cellulose acetate fiber, thermoplastic fiber, non-thermoplastic fiber, or a combination thereof. The disclosure further provides methods for forming electronic smoking articles and methods of packaging electronic smoking articles (including cartridges thereof) so as to improve moisture control of the reservoir.

6 Claims, 4 Drawing Sheets

(56) References Cited

U.S. PATENT DOCUMENTS

| | | |
|---|---|---|
| 3,398,754 A | 8/1968 | Tughan |
| 3,419,015 A | 12/1968 | Wochnowski |
| 3,424,171 A | 1/1969 | Rooker |
| 3,476,118 A | 11/1969 | Luttich |
| 4,054,145 A | 10/1977 | Berndt et al. |
| 4,131,117 A | 12/1978 | Kite et al. |
| 4,150,677 A | 4/1979 | Osborne |
| 4,190,046 A | 2/1980 | Virag |
| 4,219,032 A | 8/1980 | Tabatznik et al. |
| 4,259,970 A | 4/1981 | Green, Jr. |
| 4,284,089 A | 8/1981 | Ray |
| 4,303,083 A | 12/1981 | Burruss, Jr. |
| 4,449,541 A | 5/1984 | Mays et al. |
| 4,506,682 A | 3/1985 | Muller |
| 4,635,651 A | 1/1987 | Jacobs |
| 4,674,519 A | 6/1987 | Keritsis et al. |
| 4,708,151 A | 11/1987 | Shelar |
| 4,714,082 A | 12/1987 | Banerjee et al. |
| 4,735,217 A | 4/1988 | Gerth et al. |
| 4,756,318 A | 7/1988 | Clearman et al. |
| 4,771,795 A | 9/1988 | White et al. |
| 4,776,353 A | 10/1988 | Lilja et al. |
| 4,793,365 A | 12/1988 | Sensabaugh, Jr. et al. |
| 4,800,903 A | 1/1989 | Ray et al. |
| 4,819,665 A | 4/1989 | Roberts et al. |
| 4,821,749 A | 4/1989 | Toft et al. |
| 4,830,028 A | 5/1989 | Lawson et al. |
| 4,836,224 A | 6/1989 | Lawson et al. |
| 4,836,225 A | 6/1989 | Sudoh |
| 4,848,374 A | 7/1989 | Chard et al. |
| 4,848,376 A | 7/1989 | Lilja et al. |
| 4,874,000 A | 10/1989 | Tamol et al. |
| 4,880,018 A | 11/1989 | Graves, Jr. et al. |
| 4,887,619 A | 12/1989 | Burcham, Jr. et al. |
| 4,907,606 A | 3/1990 | Lilja et al. |
| 4,913,168 A | 4/1990 | Potter et al. |
| 4,917,119 A | 4/1990 | Potter et al. |
| 4,917,128 A | 4/1990 | Clearman et al. |
| 4,922,901 A | 5/1990 | Brooks et al. |
| 4,924,888 A | 5/1990 | Perfetti et al. |
| 4,928,714 A | 5/1990 | Shannon |
| 4,938,236 A | 7/1990 | Banerjee et al. |
| 4,941,483 A | 7/1990 | Ridings et al. |
| 4,941,484 A | 7/1990 | Clapp et al. |
| 4,945,931 A | 8/1990 | Gori |
| 4,947,874 A | 8/1990 | Brooks et al. |
| 4,947,875 A | 8/1990 | Brooks et al. |
| 4,972,854 A | 11/1990 | Kiernan et al. |
| 4,972,855 A | 11/1990 | Kuriyama et al. |
| 4,986,286 A | 1/1991 | Roberts et al. |
| 4,987,906 A | 1/1991 | Young et al. |
| 5,005,593 A | 4/1991 | Fagg |
| 5,019,122 A | 5/1991 | Clearman et al. |
| 5,022,416 A | 6/1991 | Watson |
| 5,037,459 A * | 8/1991 | Spruill .................... A24F 25/02 206/0.7 |
| 5,042,510 A | 8/1991 | Curtiss et al. |
| 5,056,537 A | 10/1991 | Brown et al. |
| 5,060,669 A | 10/1991 | White et al. |
| 5,060,671 A | 10/1991 | Counts et al. |
| 5,065,775 A | 11/1991 | Fagg |
| 5,072,744 A | 12/1991 | Luke et al. |
| 5,074,319 A | 12/1991 | White et al. |
| 5,076,296 A | 12/1991 | Nystrom et al. |
| 5,093,894 A | 3/1992 | Deevi et al. |
| 5,095,921 A | 3/1992 | Losee et al. |
| 5,097,850 A | 3/1992 | Braunshteyn et al. |
| 5,099,862 A | 3/1992 | White et al. |
| 5,099,864 A | 3/1992 | Young et al. |
| 5,103,842 A | 4/1992 | Strang et al. |
| 5,121,757 A | 6/1992 | White et al. |
| 5,129,409 A | 7/1992 | White et al. |
| 5,131,415 A | 7/1992 | Munoz et al. |
| 5,144,962 A | 8/1992 | Counts et al. |
| 5,143,097 A | 9/1992 | Sohn et al. |
| 5,146,934 A | 9/1992 | Deevi et al. |
| 5,159,940 A | 11/1992 | Hayward et al. |
| 5,159,942 A | 11/1992 | Brinkley |
| 5,179,966 A | 1/1993 | Losee et al. |
| 5,211,684 A | 5/1993 | Shannon et al. |
| 5,220,930 A | 6/1993 | Gentry |
| 5,224,498 A | 7/1993 | Deevi et al. |
| 5,228,460 A | 7/1993 | Sprinkel, Jr. et al. |
| 5,230,354 A | 7/1993 | Smith et al. |
| 5,235,992 A | 8/1993 | Sensabaugh |
| 5,243,999 A | 9/1993 | Smith |
| 5,246,018 A | 9/1993 | Deevi et al. |
| 5,249,586 A | 10/1993 | Morgan et al. |
| 5,261,424 A | 11/1993 | Sprinkel, Jr. |
| 5,269,327 A | 12/1993 | Counts et al. |
| 5,285,798 A | 2/1994 | Banerjee et al. |
| 5,293,883 A | 3/1994 | Edwards |
| 5,301,694 A | 4/1994 | Raymond |
| 5,303,720 A | 4/1994 | Banerjee et al. |
| 5,318,050 A | 6/1994 | Gonzalez-Parra et al. |
| 5,322,075 A | 6/1994 | Deevi et al. |
| 5,322,076 A | 6/1994 | Brinkley et al. |
| 5,328,759 A | 7/1994 | McCormack et al. |
| 5,339,838 A | 8/1994 | Young et al. |
| 5,345,951 A | 9/1994 | Serrano et al. |
| 5,353,813 A | 10/1994 | Deevi et al. |
| 5,357,984 A | 10/1994 | Farrier et al. |
| 5,360,023 A | 11/1994 | Blakley et al. |
| 5,369,723 A | 11/1994 | Counts et al. |
| 5,372,148 A | 12/1994 | McCafferty et al. |
| 5,377,698 A | 1/1995 | Litzinger et al. |
| 5,388,574 A | 2/1995 | Ingebrethsen et al. |
| 5,388,594 A | 2/1995 | Counts et al. |
| 5,408,574 A | 4/1995 | Deevi et al. |
| 5,435,325 A | 7/1995 | Clapp et al. |
| 5,445,169 A | 8/1995 | Brinkley et al. |
| 5,468,266 A | 11/1995 | Bensalem et al. |
| 5,468,936 A | 11/1995 | Deevi et al. |
| 5,479,948 A | 1/1996 | Counts et al. |
| 5,495,859 A | 3/1996 | Bowen et al. |
| 5,498,850 A | 3/1996 | Das |
| 5,498,855 A | 3/1996 | Deevi et al. |
| 5,499,636 A | 3/1996 | Baggett, Jr. et al. |
| 5,501,237 A | 3/1996 | Young et al. |
| 5,505,214 A | 4/1996 | Collins et al. |
| 5,515,842 A | 5/1996 | Ramseyer et al. |
| 5,530,225 A | 6/1996 | Hajaligol |
| 5,551,450 A | 9/1996 | Hemsley |
| 5,551,451 A | 9/1996 | Riggs et al. |
| 5,564,442 A | 10/1996 | MacDonald et al. |
| 5,573,692 A | 11/1996 | Das et al. |
| 5,591,368 A | 1/1997 | Fleischhauer et al. |
| 5,593,792 A | 1/1997 | Farrier et al. |
| 5,595,577 A | 1/1997 | Bensalem et al. |
| 5,596,706 A | 1/1997 | Sikk et al. |
| 5,611,360 A | 3/1997 | Tang |
| 5,613,504 A | 3/1997 | Collins et al. |
| 5,613,505 A | 3/1997 | Campbell et al. |
| 5,649,552 A | 7/1997 | Cho et al. |
| 5,649,554 A | 7/1997 | Sprinkel et al. |
| 5,659,656 A | 8/1997 | Das |
| 5,665,262 A | 9/1997 | Hajaligol et al. |
| 5,666,976 A | 9/1997 | Adams et al. |
| 5,666,977 A | 9/1997 | Higgins et al. |
| 5,666,978 A | 9/1997 | Counts et al. |
| 5,692,525 A | 12/1997 | Counts et al. |
| 5,692,526 A | 12/1997 | Adams et al. |
| 5,708,258 A | 1/1998 | Counts et al. |
| 5,711,320 A | 1/1998 | Martin |
| 5,726,421 A | 3/1998 | Fleischhauer et al. |
| 5,727,571 A | 3/1998 | Meiring et al. |
| 5,730,158 A | 3/1998 | Collins et al. |
| 5,750,964 A | 5/1998 | Counts et al. |
| 5,799,663 A | 9/1998 | Gross et al. |
| 5,816,263 A | 10/1998 | Counts et al. |
| 5,819,756 A | 10/1998 | Mielordt |
| 5,829,453 A | 11/1998 | White et al. |
| 5,865,185 A | 2/1999 | Collins et al. |
| 5,865,186 A | 2/1999 | Volsey, II |

(56) References Cited

U.S. PATENT DOCUMENTS

| | | |
|---|---|---|
| 5,878,752 A | 3/1999 | Adams et al. |
| 5,880,439 A | 3/1999 | Deevi et al. |
| 5,915,387 A | 7/1999 | Baggett, Jr. et al. |
| 5,934,289 A | 8/1999 | Watkins et al. |
| 5,954,979 A | 9/1999 | Counts et al. |
| 5,967,148 A | 10/1999 | Harris et al. |
| 6,026,820 A | 2/2000 | Baggett, Jr. et al. |
| 6,164,287 A | 2/2000 | White |
| 6,033,623 A | 3/2000 | Deevi et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,116,247 A | 9/2000 | Banyasz et al. |
| 6,119,700 A | 9/2000 | Fleischhauer et al. |
| 6,125,853 A | 10/2000 | Susa et al. |
| 6,125,855 A | 10/2000 | Nevett et al. |
| 6,125,866 A | 10/2000 | Nichols et al. |
| 6,155,268 A | 12/2000 | Takeuchi |
| 6,182,670 B1 | 2/2001 | White |
| 6,196,218 B1 | 3/2001 | Voges |
| 6,196,219 B1 | 3/2001 | Hess et al. |
| 6,216,706 B1 | 4/2001 | Kumar et al. |
| 6,289,898 B1 | 9/2001 | Fournier et al. |
| 6,349,729 B1 | 2/2002 | Pham |
| 6,357,671 B1 | 3/2002 | Cewers |
| 6,418,938 B1 | 7/2002 | Fleischhauer et al. |
| 6,446,426 B1 | 8/2002 | Sweeney et al. |
| 6,532,965 B1 | 3/2003 | Abhulimen et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,652,442 B2 | 11/2003 | Gatto |
| 6,688,313 B2 | 2/2004 | Wrenn et al. |
| 6,701,936 B2 | 3/2004 | Shafer et al. |
| 6,715,494 B1 | 4/2004 | McCoy |
| 6,730,832 B1 | 5/2004 | Dominguez et al. |
| 6,772,756 B2 | 8/2004 | Shayan |
| 6,803,545 B2 | 10/2004 | Blake et al. |
| 6,803,550 B2 | 10/2004 | Sharpe et al. |
| 6,810,883 B2 | 11/2004 | Felter et al. |
| 6,854,461 B2 | 2/2005 | Nichols |
| 6,854,470 B1 | 2/2005 | Pu |
| 6,994,096 B2 | 2/2006 | Rostami et al. |
| 7,011,096 B2 | 3/2006 | Li et al. |
| 7,017,585 B2 | 3/2006 | Li et al. |
| 7,025,066 B2 | 4/2006 | Lawson et al. |
| 7,117,867 B2 | 10/2006 | Cox et al. |
| 7,163,015 B2 | 1/2007 | Moffitt |
| 7,173,322 B2 | 2/2007 | Cox et al. |
| 7,185,659 B2 | 3/2007 | Sharpe et al. |
| 7,234,470 B2 | 6/2007 | Yang |
| 7,290,549 B2 | 11/2007 | Banerjee et al. |
| 7,293,565 B2 | 11/2007 | Griffin et al. |
| 7,392,809 B2 | 7/2008 | Larson et al. |
| 7,513,253 B2 | 4/2009 | Kobayashi et al. |
| 7,647,932 B2 | 1/2010 | Cantrell et al. |
| 7,690,385 B2 | 4/2010 | Moffitt |
| 7,692,123 B2 | 4/2010 | Baba et al. |
| 7,726,320 B2 | 6/2010 | Robinson et al. |
| 7,775,459 B2 | 8/2010 | Martens, III et al. |
| 7,810,505 B2 | 10/2010 | Yang |
| 7,832,410 B2 | 11/2010 | Hon |
| 7,845,359 B2 | 12/2010 | Montaser |
| 7,878,209 B2 | 2/2011 | Newbery et al. |
| 7,896,006 B2 | 3/2011 | Hamano et al. |
| 8,066,010 B2 | 11/2011 | Newbery et al. |
| 8,079,371 B2 | 12/2011 | Robinson et al. |
| 8,127,772 B2 | 3/2012 | Montaser |
| 8,156,944 B2 | 4/2012 | Han |
| 8,365,742 B2 | 2/2013 | Hon |
| 8,375,957 B2 | 2/2013 | Hon |
| 8,393,331 B2 | 3/2013 | Hon |
| 2002/0146242 A1 | 10/2002 | Vieira |
| 2003/0131859 A1 | 7/2003 | Li et al. |
| 2003/0226837 A1 | 12/2003 | Blake et al. |
| 2004/0020500 A1 | 2/2004 | Wrenn et al. |
| 2004/0129280 A1 | 7/2004 | Woodson et al. |
| 2004/0149296 A1 | 8/2004 | Rostami et al. |
| 2004/0200488 A1 | 10/2004 | Felter et al. |
| 2004/0224435 A1 | 11/2004 | Shibata et al. |
| 2004/0226568 A1 | 11/2004 | Takeuchi et al. |
| 2004/0255965 A1 | 12/2004 | Perfetti et al. |
| 2005/0016549 A1 | 1/2005 | Banerjee et al. |
| 2005/0016550 A1 | 1/2005 | Katase |
| 2005/0066986 A1 | 3/2005 | Nestor et al. |
| 2005/0151126 A1 | 7/2005 | Yamakawa et al. |
| 2005/0172976 A1 | 8/2005 | Newman et al. |
| 2005/0235991 A1 | 10/2005 | Nichols et al. |
| 2005/0274390 A1 | 12/2005 | Banerjee et al. |
| 2006/0016453 A1 | 1/2006 | Kim |
| 2006/0032501 A1 | 2/2006 | Hale et al. |
| 2006/0070633 A1 | 4/2006 | Rostami et al. |
| 2006/0162733 A1 | 7/2006 | McGrath et al. |
| 2006/0185687 A1 | 8/2006 | Hearn et al. |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2007/0283972 A1 | 12/2007 | Monsees et al. |
| 2008/0092912 A1 | 4/2008 | Robinson et al. |
| 2008/0149118 A1 | 6/2008 | Oglesby et al. |
| 2008/0245377 A1 | 10/2008 | Marshall et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0065010 A1 | 3/2009 | Shands |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0260641 A1 | 10/2009 | Monsees et al. |
| 2009/0260642 A1 | 10/2009 | Monsees et al. |
| 2009/0272379 A1 | 11/2009 | Thorens et al. |
| 2009/0283103 A1 | 11/2009 | Nielsen et al. |
| 2009/0293892 A1 | 12/2009 | Williams et al. |
| 2009/0320863 A1 | 12/2009 | Fernando et al. |
| 2009/0324206 A1 | 12/2009 | Young et al. |
| 2010/0006113 A1 | 1/2010 | Urtsev et al. |
| 2010/0024834 A1 | 2/2010 | Oglesby et al. |
| 2010/0043809 A1 | 2/2010 | Magnon |
| 2010/0059070 A1 | 3/2010 | Potter et al. |
| 2010/0059073 A1 | 3/2010 | Hoffmann et al. |
| 2010/0065075 A1 | 3/2010 | Banerjee et al. |
| 2010/0083959 A1 | 4/2010 | Siller |
| 2010/0163063 A1 | 7/2010 | Fernando et al. |
| 2010/0200006 A1 | 8/2010 | Robinson et al. |
| 2010/0229881 A1 | 9/2010 | Hearn |
| 2010/0242974 A1 | 9/2010 | Pan |
| 2010/0242976 A1 | 9/2010 | Katayama et al. |
| 2010/0258139 A1 | 10/2010 | Onishi et al. |
| 2010/0300467 A1 | 12/2010 | Kuistilla et al. |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0073121 A1 | 3/2011 | Levin et al. |
| 2011/0088707 A1 | 4/2011 | Hajaligol |
| 2011/0094523 A1 | 4/2011 | Thorens et al. |
| 2011/0120480 A1 | 5/2011 | Brenneise |
| 2011/0126847 A1 | 6/2011 | Zuber et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0162663 A1 | 7/2011 | Bryman |
| 2011/0168194 A1 | 7/2011 | Hon |
| 2011/0180082 A1 | 7/2011 | Banerjee et al. |
| 2011/0226236 A1* | 9/2011 | Buchberger ......... A61M 11/041 128/200.23 |
| 2011/0265806 A1 | 11/2011 | Alarcon et al. |
| 2011/0309157 A1 | 12/2011 | Yang et al. |

(56) References Cited

U.S. PATENT DOCUMENTS

| | | |
|---|---|---|
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0231464 A1 | 9/2012 | Yu et al. |
| 2012/0279512 A1 | 11/2012 | Hon |
| 2012/0318882 A1 | 12/2012 | Abehasera |
| 2013/0081642 A1 | 4/2013 | Safari |
| 2013/0160780 A1 | 6/2013 | Matsumoto et al. |
| 2013/0306084 A1 | 11/2013 | Flick |
| 2013/0340775 A1 | 12/2013 | Juster et al. |
| 2014/0000638 A1 | 1/2014 | Sebastian et al. |
| 2014/0109905 A1 | 4/2014 | Yamada et al. |
| 2014/0238424 A1 | 8/2014 | Macko et al. |
| 2014/0338680 A1 | 11/2014 | Abramov et al. |
| 2014/0345633 A1 * | 11/2014 | Talon ................. A24F 47/008 131/329 |
| 2015/0027454 A1 | 1/2015 | Li et al. |

FOREIGN PATENT DOCUMENTS

| | | |
|---|---|---|
| CA | 2 752 255 | 8/2010 |
| CA | 2 840 870 | 2/2013 |
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| EP | 2 468 116 | 6/2012 |
| EP | 2 589 306 | 8/2013 |
| GB | 1444461 | 7/1976 |
| GB | 2469850 | 11/2010 |
| WO | WO 1986/02528 | 5/1986 |
| WO | WO 91/18636 | 12/1991 |
| WO | WO 1997/48293 | 12/1997 |
| WO | WO 02/37990 | 5/2002 |
| WO | WO 2004/043175 | 5/2004 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/091593 | 8/2010 |
| WO | WO 2010/118644 | 10/2010 |
| WO | WO 2010/140937 | 12/2010 |
| WO | WO 2011/010334 | 1/2011 |
| WO | WO 2011/081558 | 7/2011 |
| WO | WO 2012/072762 | 6/2012 |
| WO | WO 2013/034460 | 3/2013 |
| WO | WO 2013/089551 | 6/2013 |
| WO | WO 2013/098395 | 7/2013 |

* cited by examiner

ELECTRONIC SMOKING ARTICLE WITH IMPROVED STORAGE OF AEROSOL PRECURSOR COMPOSITIONS

CROSS-REFERENCE TO RELATED APPLICATIONS

The present application is a divisional of U.S. application Ser. No. 14/158,264 filed Jan. 17, 2014, which is incorporated by reference herein in its entirety.

FIELD OF THE DISCLOSURE

The present disclosure relates to aerosol delivery devices such as smoking articles, and more particularly to means for providing an indication of a status of such devices to a user thereof. The smoking articles may be configured to heat a material, which may be made or derived from tobacco or otherwise incorporate tobacco, to form an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. patent application Ser. No. 13/432,406, filed Mar. 28, 2012, U.S. patent application Ser. No. 13/536,438, filed Jun. 28, 2012, U.S. patent application Ser. No. 13/602,871, filed Sep. 4, 2012, and U.S. patent application Ser. No. 13/647,000, filed Oct. 8, 2012, which are incorporated herein by reference.

Certain tobacco products that have employed electrical energy to produce heat for smoke or aerosol formation, and in particular, certain products that have been referred to as electronic cigarette products, have been commercially available throughout the world. Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; COHITA™, COLIBRI™, ELITE CLASSIC™, MAGNUM™, PHANTOM™ and SENSE™ by Epuffer® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; GREEN SMOKE® by Green Smoke Inc. USA; GREENARETTE™ by Greenarette LLC; HALLIGAN™, HENDU™, JET™, MAXXQ™ PINK™ and PITBULL™ by Smoke Stik®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC and VUSE® by R. J. Reynolds Vapor Company. Yet other electrically powered aerosol delivery devices, and in particular those devices that have been characterized as so-called electronic cigarettes, have been marketed under the tradenames BLU™; COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP® and SOUTH BEACH SMOKE™.

It would be desirable to provide a smoking article that employs heat produced by electrical energy to provide the sensations of cigarette, cigar, or pipe smoking, that does so without combusting tobacco to any significant degree, that does so without the need of a combustion heat source, and that does so without necessarily delivering considerable quantities of incomplete combustion and pyrolysis products. Further, advances with respect to manufacturing electronic smoking articles would be desirable.

BRIEF SUMMARY

The present disclosure provides smoking articles and related components and methods of manufacture and packaging. The disclosure particularly provides for devices and methods that can control transfer of moisture to and from a reservoir, particularly a reservoir comprising a woven or nonwoven fabric, such as formed from cellulose acetate or a similar fiber or fibers.

In some embodiments, the present disclosure provides an electronic smoking article. The electronic smoking article can comprise a housing and a reservoir within the housing that is configured to hold an aerosol precursor fluid. The reservoir can comprise a woven or nonwoven fabric exhibiting specific properties that are useful in controlling moisture absorption and/or adsorption or, additionally or in the alternative, controlling moisture release. Moisture release particularly may occur in known devices in the form of sweating, wherein excess liquid, particularly water, may be released from a reservoir during storage or other handling, such release not being related to aerosolization via activation of an associated heater. Such release of liquid within the housing can be undesirable and may result in deleterious effects on one or more components of the electronic smoking article and/or may result in leakage from the housing to the surrounding environment, such as within packaging or onto a consumer.

In some embodiments, a woven or nonwoven fabric may be useful in that it exhibits a basis weight that can provide a useful effect in liquid control. For example, a woven or nonwoven fabric used in a reservoir according to the present disclosure can have a basis weight of about 120 gsm or greater, particularly about 130 or greater. Further useful basis weights are further disclosed herein. In some embodiments, a plurality of layers of woven fabrics, non-woven fabrics, or combinations thereof may be utilized, the combination of the layers exhibiting the basis weight described herein.

In some embodiments, a reservoir in a smoking article according to the present disclosure may be substantially shaped as a cylinder having a hollow interior portion (although other shapes are also encompassed as otherwise disclosed herein). Although a variety of fibers may be used in forming a woven or nonwoven fabric according to the present disclosure, the woven or nonwoven fabric particularly may comprise cellulose acetate. A woven or nonwoven fabric used in a reservoir according to the present disclosure can have a thickness (e.g., the thickness of a cylinder wall) of about 1 mm to about 4 mm.

Utilizing reservoir fabrics having a basis weight as described herein can be useful in relation to preventing capillary loses. For example, when a liquid-loaded fabric is in close proximity to another material, liquid may pass from the fabric to the other material through capillary action. Capillary loses, such as between a reservoir and a wall of an electronic smoking article, can be reduced according to the present disclosure.

In some embodiments, it can be useful for the aerosol precursor composition (particularly a liquid composition) to be applied to the reservoir in a limited content. More particularly, the amount of the aerosol precursor composition applied to the reservoir may be defined in relation to the saturation capacity of the reservoir. For example, reservoir materials according to some embodiments of the present disclosure can have a saturation capacity of up to about 2,000% by weight of the reservoir, particularly about 800% to about 2,000% by weight. The weight of aerosol precursor fluid in the reservoir relative to the saturation capacity of the reservoir can be no greater than about 80% or no greater than about 60%. In other words, the reservoir may be loaded with a weight of aerosol precursor fluid that is no greater than about 80% of the saturation capacity of the reservoir.

It also may be useful to limit the water content of an aerosol precursor composition that is added to a reservoir. For example, an aerosol precursor composition added to reservoir according to the present disclosure can include water in amount that is greater than about 0.1% and is less than about 15% by weight.

An electronic smoking article according to the present disclosure further can comprise an atomizer. In some embodiments, an atomizer may comprise a continuous, elongated wick having two opposing ends, a heater in connection with the wick and positioned at about a midpoint thereof, and electrically conducting terminals positioned in physical contact with the wick and in electrical connection with the heater.

In some embodiments, a combined housing and reservoir may define a cartridge body. As such, a smoking article according to the present disclosure further can comprise a second housing that includes a power source and/or a controller. The second housing thus may define a control body or a power body. The second housing defining the control body or power body can be removably attached to the housing comprising the reservoir (i.e., the cartridge body).

In further embodiments, an electronic smoking article according to the present disclosure may comprise a housing having an air inlet adapted for entry of air into the housing and an air outlet adapted for exit of a formed aerosol, the inlet and the outlet having an air passage therebetween. The smoking article also can comprise a reservoir within the housing that is configured to hold an aerosol precursor fluid and a heater in fluid communication with the reservoir. The heater may be positioned at least partially within the air passage. Still further, the smoking article can include a first check valve positioned at the air inlet and a second check valve positioned at the air outlet. In particular, the first check valve and the second check valve can be adapted to open only in the direction of air flow from the air inlet to the air outlet. Specifically, the first check valve and the second check valve can both be one way check valves. In particular embodiments, at least one of the first check valve and the second check valve can form a seal that is impermeable to liquid and aerosol when in the closed position.

In some embodiments, a smoking article according to the present disclosure may comprise a housing including a reservoir that is configured to hold an aerosol precursor fluid. The smoking article also can comprise an absorptive material that is separate from the reservoir. The absorptive material specifically may be a lining on an interior wall of the housing. In some embodiments, the absorptive lining may be located only at one or both of the first end and the second end of the housing. The absorptive material can be adapted to absorb any free liquid within the housing—e.g., any liquid that escapes from the reservoir or liquid vapor or the like that may enter the housing. Specifically, the absorptive material can be configured to preferentially absorb hydrophilic liquids, particularly water. The presence of a substantially dry, absorptive material in the housing with a reservoir that is already filled with an aerosol precursor composition can be beneficial in that ambient water vapor entering the housing may be preferentially absorbed by the absorptive material rather than the reservoir. Further, any sweating by the reservoir may be absorbed by the absorptive material rather than escaping from the housing or freely moving within the housing where it may contact other parts, such as the heater.

In further embodiments, a reservoir utilized in a device according to the present disclosure may be enclosed by a layer within the housing of the device. For example, the layer can be a liquid and/or vapor impermeable container, such as a bag. The container can include a sealable opening through which a liquid transport element can extend to deliver liquid from the reservoir inside the container to a heater outside the container. In other embodiments, the layer can be formed of a material that is liquid impermeable but vapor permeable. As such, liquid can be prevented from passing through the container, but entraining air can be allowed to pass into the container, and the vapor entrained in the air (e.g., an aerosol) can be allowed to pass out of the container.

In still other embodiments, a reservoir can comprise a container, tank, or the like in which the aerosol precursor composition is contained and which is openable and closable for release of the aerosol precursor composition. For example, a valve can be provided to allow exit of aliquots of the aerosol precursor composition only immediately prior to vaporization.

In some embodiments, the present disclosure further can provide a method of assembling an electronic smoking article. For example, the method can comprise providing a reservoir that is configured to hold an aerosol precursor fluid, the reservoir comprising a woven or nonwoven fabric; inserting the reservoir into a hollow housing; and adding the aerosol precursor fluid to the reservoir before or after said inserting. In certain embodiments, the assembly can be carried out under an ambient relative humidity that is below a defined value. For example, assembly can be carried out under an ambient relative humidity of no greater than about 40%. In some embodiments, the assembly can be carried out under an inert atmosphere. For example, the inert atmosphere can be a noble gas atmosphere, such as an argon atmosphere.

In some embodiments, the assembly method can comprise engaging an open end of the housing with a cap. The method specifically can comprise crimping the housing to the cap so as to establish a non-hermetic seal between the housing and the cap that prevents passage of liquid (specifically water) therethrough but may allow passage of gas or vapor therethrough.

In still further embodiments, the present disclosure provides methods of packaging an electronic cigarette or a component thereof (e.g., a cartridge body). For example, the method can comprise: providing the cartridge with a reservoir therein, the reservoir comprising a woven or nonwoven fabric and having an aerosol precursor fluid therein; and positioning the cartridge within a non-hermetically sealed display package formed of a material that is substantially impermeable to water vapor. In various embodiments, the packaging method further can be characterized in that at least one of the following conditions is met: any opening in the non-hermetically sealed display package is covered with a water-tight sealing tape; a desiccant is included within the non-hermetically sealed display package; a humidity control device is included within the non-hermetically sealed display package, the humidity control device being adapted to maintain a relative humidity within the package of about 5% to about 50%; and the cartridge is enclosed by a polymeric barrier within the non-hermetically sealed display package. In embodiments including a polymeric barrier, the barrier can be lining the interior of the non-hermetically sealed display package. In particular embodiments, the polymeric barrier can be a blister package encasing the cartridge.

BRIEF DESCRIPTION OF THE FIGURES

Figure 1:
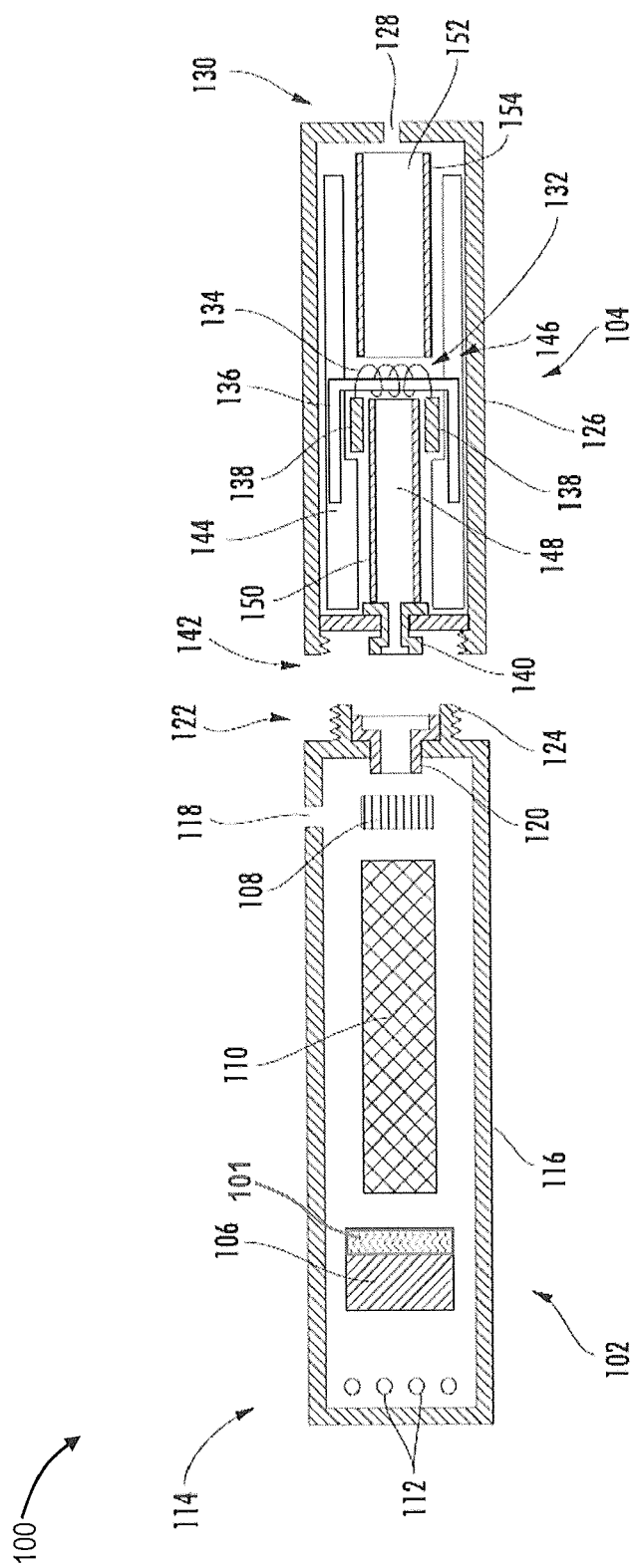
Figure 2:
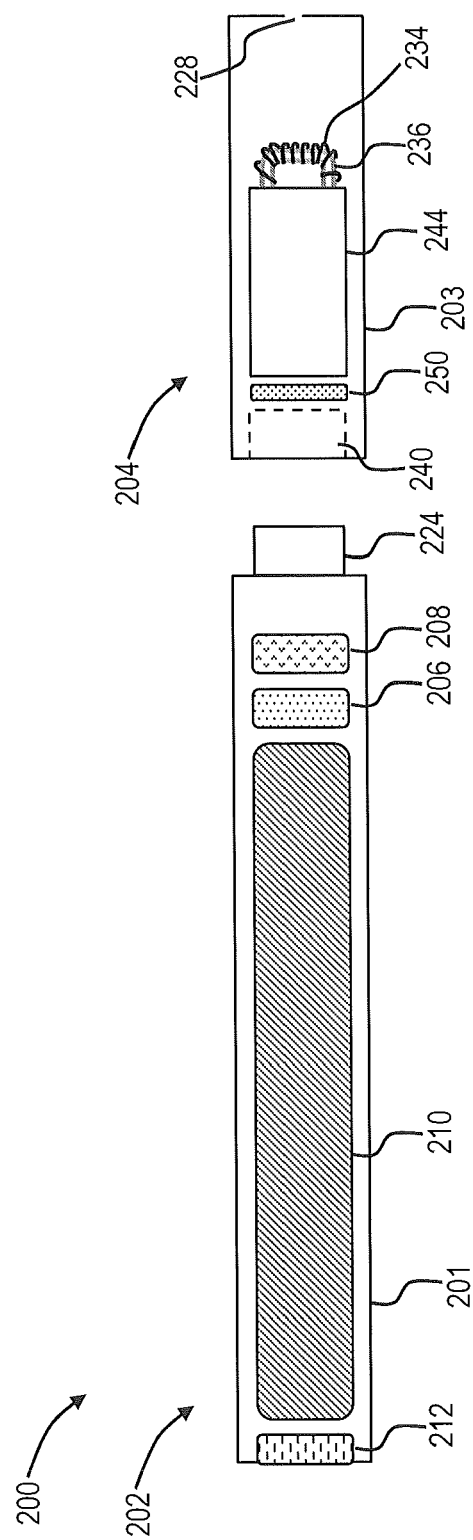
Figure 3:
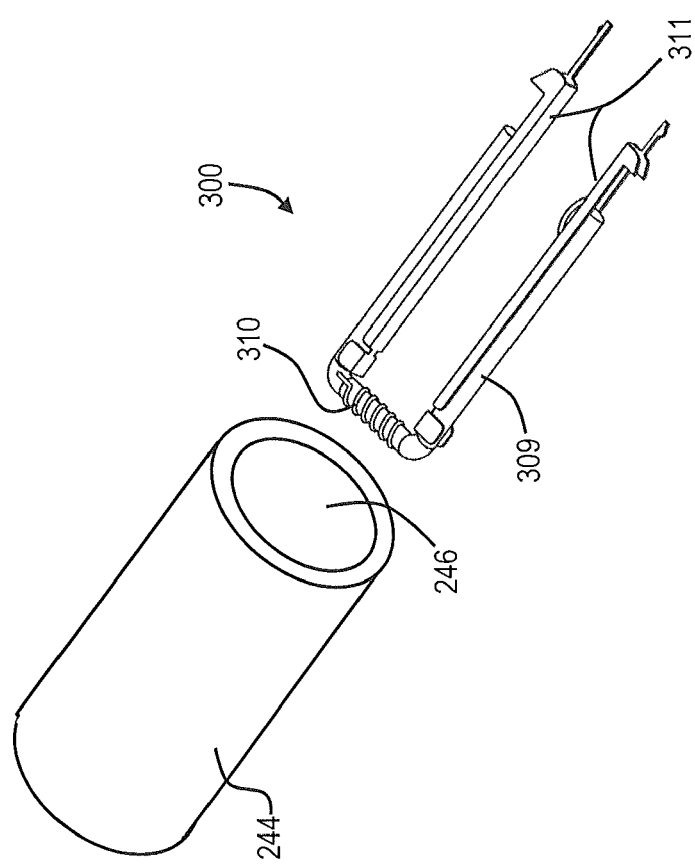
Figure 4:
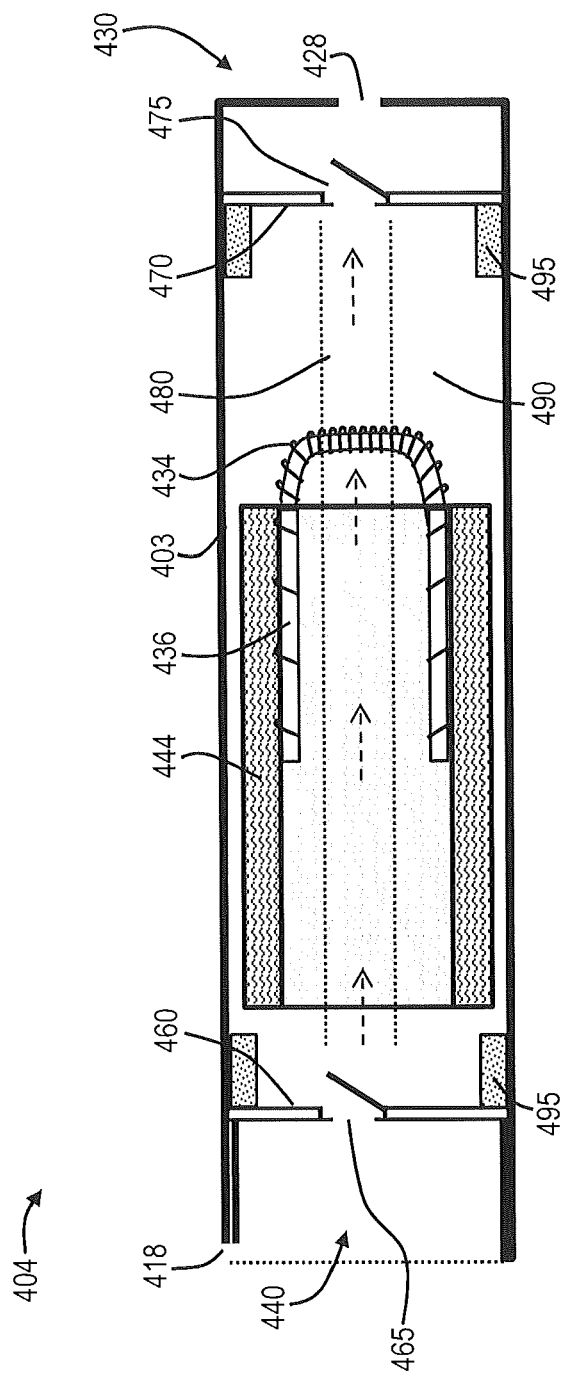

Having thus described the disclosure in the foregoing general terms, reference will now be made to the accompanying drawings, which are not necessarily drawn to scale, and wherein:

FIG. 1 illustrates a sectional view through an embodiment of a smoking article according to an embodiment of the present disclosure;

FIG. 2 illustrates a sectional view through an embodiment of a smoking article according to a further embodiment of the present disclosure;

FIG. 3 illustrates an exploded view of an atomizer according to an embodiment of the present disclosure including a reservoir, a wick, and a heater; and FIG. 4 illustrates a sectional view through an embodiment of a cartridge according to the present disclosure.

DETAILED DESCRIPTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure provides descriptions of aerosol delivery devices or smoking articles, such as so-called "e-cigarettes." It should be understood that the mechanisms, components, features, and methods may be embodied in many different forms and associated with a variety of articles.

In this regard, the present disclosure provides descriptions of aerosol delivery devices that use electrical energy to heat a material (preferably without pyrolyzing or combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of pyrolysis or combustion of any component of that article or device. The aerosol delivery device may not produce smoke in the sense of the aerosol resulting from by-products of combustion or pyrolysis of tobacco, but rather, that the article or device may yield vapors (including vapors within aerosols that can be considered to be visible aerosols that might be considered to be described as smoke-like) resulting from volatilization or vaporization of certain components of the article or device. In highly preferred embodiments, aerosol delivery devices may incorporate tobacco and/or components derived from tobacco.

Aerosol delivery devices of the present disclosure also can be characterized as being vapor-producing articles, smoking articles, or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer body or shell. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. In one embodiment, all of the components of the aerosol delivery device are contained within one outer body or shell. Alternatively, an aerosol delivery device can comprise two or more shells that are joined and are separable. For example, an aerosol delivery device can possess at one end a control body comprising an outer body or shell containing one or more reusable components (e.g., a rechargeable battery and various electronics for controlling the operation of that article), and at the other end and removably attached thereto an outer body or shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic aerosol delivery devices, such as those representative products listed in the background art section of the present disclosure.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microcontroller), a heater or heat generation component (e.g., an electrical resistance heating element or component commonly referred to as an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the article such that aerosol generated can be withdrawn therefrom upon draw). Exemplary formulations for aerosol precursor materials that may be used according to the present disclosure are described in U.S. Pat. Pub. No. 2013/0008457 to Zheng et al., the disclosure of which is incorporated herein by reference in its entirety.

Alignment of the components within the aerosol delivery device can vary. In specific embodiments, the aerosol precursor composition can be located near an end of the article (e.g., within a cartridge, which in certain circumstances can be replaceable and disposable), which may be proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various aerosol delivery device components can be appreciated upon consideration of the commercially available electronic aerosol delivery devices, such as those representative products listed in the background art section of the present disclosure.

An aerosol delivery device incorporates a battery or other electrical power source to provide current flow sufficient to provide various functionalities to the article, such as resistive heating, powering of control systems, powering of indicators, and the like. The power source can take on various embodiments. Preferably, the power source is able to deliver sufficient power to rapidly heat the heating member to provide for aerosol formation and power the article through use for the desired duration of time. The power source preferably is sized to fit conveniently within the aerosol delivery device so that the aerosol delivery device can be easily handled; and additionally, a preferred power source is of a sufficiently light weight to not detract from a desirable smoking experience.

One example embodiment of an aerosol delivery device 100 is provided in FIG. 1. As seen in the cross-section illustrated therein, the aerosol delivery device 100 can comprise a control body 102 and a cartridge 104 that can be permanently or detachably aligned in a functioning relationship. Although a threaded engagement is illustrated in FIG. 1, it is understood that further means of engagement may be employed, such as a press-fit engagement, interference fit, a magnetic engagement, or the like.

In specific embodiments, one or both of the control body 102 and the cartridge 104 may be referred to as being disposable or as being reusable. For example, the control body may have a replaceable battery or a rechargeable battery and thus may be combined with any type of recharging technology, including connection to a typical electrical outlet, connection to a car charger (i.e., cigarette lighter receptacle), and connection to a computer, such as through a universal serial bus (USB) cable. For example, an adaptor including a USB connector at one end and a control body connector at an opposing end is disclosed in U.S. patent application Ser. No. 13/840,264, filed Mar. 15, 2013, which is incorporated herein by reference in its entirety. Further, in some embodiments the cartridge may comprise a single-use cartridge, as disclosed in U.S. patent application Ser. No. 13/603,612, filed Sep. 5, 2012, which is incorporated herein by reference in its entirety.

In the exemplified embodiment, the control body 102 includes a control component 106 (e.g., a microcontroller), a flow sensor 108, and a battery 110, which can be variably aligned, and can include a plurality of indicators 112 at a distal end 114 of an outer body 116. The indicators 112 can be provided in varying numbers and can take on different shapes and can even be an opening in the body (such as for release of sound when such indicators are present). In the exemplified embodiment, a haptic feedback component 101 is included with the control component 106. As such, the haptic feedback component may be integrated with one or more components of a smoking article for providing vibration or like tactile indication of use or status to a user. See, for example, the disclosure of U.S. patent application Ser. No. 13/946,309, filed Jul. 19, 2013, which is incorporated herein by reference in its entirety.

An air intake 118 may be positioned in the outer body 116 of the control body 102. A coupler 120 also is included at the proximal attachment end 122 of the control body 102 and may extend into a control body projection 124 to allow for ease of electrical connection with an atomizer or a component thereof, such as a resistive heating element (described below) when the cartridge 104 is attached to the control body. Although the air intake 118 is illustrated as being provided in the outer body 116, in another embodiment the air intake may be provided in a coupler as described, for example, in U.S. patent application Ser. No. 13/841,233; Filed Mar. 15, 2013.

The cartridge 104 includes an outer body 126 with a mouth opening 128 at a mouthend 130 thereof to allow passage of air and entrained vapor (i.e., the components of the aerosol precursor composition in an inhalable form) from the cartridge to a consumer during draw on the aerosol delivery device 100. The aerosol delivery device 100 may be substantially rod-like or substantially tubular shaped or substantially cylindrically shaped in some embodiments. In other embodiments, further shapes and dimensions are encompassed—e.g., a rectangular or triangular cross-section, or the like.

The cartridge 104 further includes an atomizer 132 comprising a resistive heating element 134 (e.g., a wire coil) configured to produce heat and a liquid transport element 136 (e.g., a wick) configured to transport a liquid. Various embodiments of materials configured to produce heat when electrical current is applied therethrough may be employed to form the resistive heating element 134. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), carbon graphite, and ceramic (e.g., a positive temperature coefficient ceramic). Further to the above, representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties.

Electrically conductive heater terminals 138 (e.g., positive and negative terminals) at the opposing ends of the heating element 134 are configured to direct current flow through the heating element and configured for attachment to the appropriate wiring or circuit (not illustrated) to form an electrical connection of the heating element with the battery 110 when the cartridge 104 is connected to the control body 102. Specifically, a plug 140 may be positioned at a distal attachment end 142 of the cartridge 104. When the cartridge 104 is connected to the control body 102, the plug 140 engages the coupler 120 to form an electrical connection such that current controllably flows from the battery 110, through the coupler and plug, and to the heating element 134. The outer body 126 of the cartridge 104 can continue across the distal attachment end 142 such that this end of the cartridge is substantially closed with the plug 140 protruding therefrom.

A reservoir may utilize a liquid transport element to transport an aerosol precursor composition to an aerosolization zone. One such example is shown in FIG. 1. As seen therein, the cartridge 104 includes a reservoir layer 144 comprising layers of nonwoven fibers formed into the shape of a tube encircling the interior of the outer body 126 of the cartridge, in this embodiment. An aerosol precursor composition is retained in the reservoir layer 144. Liquid components, for example, can be sorptively retained by the reservoir layer 144. The reservoir layer 144 is in fluid connection with a liquid transport element 136. The liquid transport element 136 transports the aerosol precursor composition stored in the reservoir layer 144 via capillary action to an aerosolization zone 146 of the cartridge 104. As illustrated, the liquid transport element 136 is in direct contact with the heating element 134 that is in the form of a metal wire coil in this embodiment.

It is understood that an aerosol delivery device that can be manufactured according to the present disclosure can encompass a variety of combinations of components useful in forming an electronic aerosol delivery device. Reference is made for example to the reservoir and heater system for controllable delivery of multiple aerosolizable materials in an electronic smoking article disclosed in U.S. patent application Ser. No. 13/536,438, filed Jun. 28, 2012, which is incorporated herein by reference in its entirety. Further, U.S. patent application Ser. No. 13/602,871, filed Sep. 4, 2012, discloses an electronic smoking article including a microheater, and which is incorporated herein by reference in its entirety.

Reference also is made to U.S. Pat. Pub. No. 2013/0213419, which discloses a ribbon of electrically resistive mesh material that may be wound around a wick, and to U.S. Pat. Pub. No. 2013/0192619, which discloses a heater coil about a wick wherein the coil windings have substantially uniform spacing between each winding. In certain embodiments according to the present disclosure, a heater may comprise a metal wire, which may be wound with a varying pitch around a liquid transport element, such as a wick. An exemplary variable pitch heater that may be used according to the present disclosure is described in U.S. patent application Ser. No. 13/827,994, filed Mar. 14, 2013, the disclosure of which is incorporated herein by reference in its entirety.

Reference also is made to a liquid supply reservoir formed of an elastomeric material and adapted to be manually compressed so as to pump liquid material therefrom, as disclosed in U.S. Pat. Pub. No. 2013/0213418. In certain embodiments according to the present disclosure, a reservoir may particularly be formed of a fibrous material, such as a fibrous mat or tube that may absorb or adsorb a liquid material.

In another embodiment substantially the entirety of the cartridge may be formed from one or more carbon materials, which may provide advantages in terms of biodegradability and absence of wires. In this regard, the heating element may comprise a carbon foam, the reservoir may comprise carbonized fabric, and graphite may be employed to form an electrical connection with the battery and controller. Such carbon cartridge may be combined with one or more elements as described herein for providing illumination of the cartridge in some embodiments. An example embodiment of a carbon-based cartridge is provided in U.S. patent application Ser. No. 13/432,406; filed Mar. 28, 2012, which is incorporated herein by reference in its entirety.

In use, when a user draws on the article 100, the heating element 134 is activated (e.g., such as via a flow sensor), and the components for the aerosol precursor composition are vaporized in the aerosolization zone 146. Drawing upon the mouthend 130 of the article 100 causes ambient air to enter the air intake 118 and pass through the central opening in the coupler 120 and the central opening in the plug 140. In the cartridge 104, the drawn air passes through an air passage 148 in an air passage tube 150 and combines with the formed vapor in the aerosolization zone 146 to form an aerosol. The aerosol is whisked away from the aerosolization zone 146, passes through an air passage 152 in an air passage tube 154, and out the mouth opening 128 in the mouthend 130 of the article 100.

The various components of an aerosol delivery device according to the present disclosure can be chosen from components described in the art and commercially available. Examples of batteries that can be used according to the disclosure are described in U.S. Pat. App. Pub. No. 2010/0028766, the disclosure of which is incorporated herein by reference in its entirety.

An exemplary mechanism that can provide puff-actuation capability includes a Model 163PC01D36 silicon sensor, manufactured by the MicroSwitch division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Further description of current regulating circuits and other control components, including microcontrollers that can be useful in the present aerosol delivery device, are provided in U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties.

Reference also is made to International Publications WO 2013/098396, WO 2013/098397, and WO 2013/098398, which describe controllers configured to control power supplied to a heater element from a power source as a means to monitor a status of the device, such as heater temperature, air flow past a heater, and presence of an aerosol forming material near a heater. In particular embodiments, the present disclosure provides a variety of control systems adapted to monitor status indicators, such as through communication of a microcontroller in a control body and a microcontroller or other electronic component in a cartridge component.

The aerosol precursor, which may also be referred to as an aerosol precursor composition or a vapor precursor composition, can comprise one or more different components. For example, the aerosol precursor can include a polyhydric alcohol (e.g., glycerin, propylene glycol, or a mixture thereof). Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference. In some embodiments, the aerosol precursor fluid can include water in an amount that is greater than about 0.1% and less than about 15% by weight. For example, water can be present in an amount of about 1% by weight to about 15% by weight, about 2% by weight to about 14% by weight, or about 5% by weight to about 13% by weight.

Still further components can be utilized in the aerosol delivery device of the present disclosure. For example, U.S. Pat. No. 5,154,192 to Sprinkel et al. discloses indicators that may be used with smoking articles; U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. App. Pub. No. 2010/0163063 by Fernando et al. discloses identification systems for smoking devices; U.S. Pat. App. Pub. No. 2013/0213418 to Tucker et al. discloses means for aerosol production through heating of a capillary tube; WO 2010/003480 to Flick discloses a fluid flow sensing system indicative of a puff in an aerosol generating system; and WO 2013/102612 to Greim et al. discloses a charging device for an electronic smoking article, all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,388,574 to Ingebrethsen; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. No. 8,156,944 to Hon; U.S. Pat. No. 8,365,742 to Hon; U.S. Pat. No. 8,375,957 to Hon; U.S. Pat. No. 8,393,331 to Hon; U.S. Pat. App. Pub. Nos. 2006/0196518 and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; WO 2010/091593 to Hon; WO 2013/089551 to Foo; WO 2013/083631 and WO 2013/083634 to Dubief et al.; WO 2013/098396 to Talon et al.; WO 2013/102611 to Greim et al.; U.S. Pat. App. Pub. No. 2013/0192615 to Tucker et al.; U.S. Pat. App. Pub. No. 2013/0192621 to Li et al.; and U.S. patent application Ser. No. 13/841,233, filed Mar. 15, 2013, each of which is incorporated herein by reference in its entirety. A variety of the materials disclosed by the foregoing documents may be incorporated into the present devices in various embodiments, and all of the foregoing disclosures are incorporated herein by reference in their entireties.

The foregoing description of use of the article can be applied to the various embodiments described herein through minor modifications, which can be apparent to the person of skill in the art in light of the further disclosure provided herein. The above description of use, however, is not intended to limit the use of the article but is provided to comply with all necessary requirements of disclosure of the present disclosure.

A further exemplary embodiment of a smoking article 200 according to the present disclosure is shown in FIG. 2. As illustrated therein, a control body 202 can be formed of a housing 201 that can include a control component 206, a flow sensor 208, a battery 210, and an LED 212. A cartridge 204 can be formed of a housing 203 enclosing a reservoir 244 that is in fluid communication with a transport element 236 adapted to wick or otherwise transport an aerosol precursor composition stored in the reservoir to a heater 234. An opening 228 may be present in the cartridge housing 203 to allow for egress of formed aerosol from the cartridge 204. Such components are representative of the components that may be present in a cartridge and are not intended to limit the scope of cartridge components that are encompassed by the present disclosure. The cartridge 204 may be adapted to engage the control body 202 through a press-fit engagement between the control body projection 224 and the cartridge receptacle 240. Such engagement can facilitate a stable connection between the control body 202 and the cartridge 204 as well as establish an electrical connection between the battery 210 and control component 206 in the control body and the heater 234 in the cartridge. The cartridge 204 also may include one or more electronic components 250, which may include an IC, a memory component, a sensor, or the like. The electronic component 250 may be adapted to communicate with the control component 206.

In various embodiments, the present disclosure particularly can provide for improved control of fluid passage (particularly water, including water vapor) into and/or out of a housing in which a reservoir is contained such as, for example, a smoking article (and particularly a cartridge thereof). For example, in some embodiments, the present disclosure can provide for improving retention of an aerosol precursor composition in a housing, particularly within its reservoir, and thus prevent or reduce leaking of the liquid out of the housing. In some embodiments, the present disclosure can provide for preventing or reducing ingress of moisture (e.g., water vapor) into a housing. In some embodiments, the present disclosure can provide for preventing or reducing dilution of an aerosol precursor composition in a reservoir such as may occur through absorption of water vapor from air. Such moisture control can relate to the nature of the smoking article itself, methods of manufacturing of the smoking article, methods of packaging of the smoking article, and combinations thereof.

Returning to FIG. 2, the cartridge 204 can be substantially tubular in shape. As such, the reservoir 244 likewise can be substantially tubular in shape (see FIG. 3) and can be formed of a reservoir wall 245. The reservoir 244 can be substantially rod-like or substantially tubular shaped or substantially cylindrically shaped. Thus, the reservoir 244 can have a diameter such that the reservoir can be adapted to fit within the housing forming cartridge 204. The reservoir 244 can be formed from a plurality of combined layers that can be concentric or overlapping. For example, the reservoir 244 can be a continuous sheet of material that is rolled to form the hollow tube. The reservoir 244 can be a woven or non-woven material. For example, the reservoir 244 may be a mat of nonwoven material. In other embodiments, the reservoir 244 can be substantially a unitary component. For example, the reservoir 244 can be shaped or molded so as to be a singular element in the form of a substantially hollow tube that is substantially continuous in composition across the length and thickness thereof. The reservoir 244 can be rigid or semi-rigid. If desired, one or more additional components of a smoking article according to the present disclosure can be accommodated within or around the reservoir 244. While the reservoir 244 is shown in the cartridge 204 portion of a smoking article in FIG. 2, one skilled in the art will appreciate that the reservoir can be positioned within any portion of a smoking article so as not to impede the storage and delivery of an aerosol precursor composition stored therein.

In certain embodiments, a reservoir according to the present disclosure can be provided in a form such that at least part of the hollow interior thereof is shaped and dimensioned to accommodate one or more further components of the smoking article. In some embodiments, the term "shaped and dimensioned" can indicate that a wall of the hollow interior includes one or more indentations or protrusions that cause the interior to have a shape that is other than substantially smooth and continuous. In other embodiments, the hollow nature of the reservoir can be sufficient to allow for accommodation of further components of the smoking article without the need for formation of cavities or protrusions. This particularly can facilitate ease of assembly of the smoking article and can maximize the reservoir volume while also providing sufficient space for aerosol formation. As seen in FIG. 3, the exterior surface of the reservoir 244 can be adapted to conform to the interior surface of the housing forming the cartridge 204. The reservoir 244 can have an inner surface that defines a central cavity 246 of the reservoir. In some embodiments, the inner surface of the reservoir may be characterized as being shaped and dimensioned to accommodate an atomizer 300 in that the atomizer can be positioned with the central cavity 246 such that a portion of the atomizer is in fluid connection with the reservoir.

The atomizer 300 can comprise a heater, a liquid transport element, and electrically conducting terminals (which may be optional). In the illustrated embodiments, the liquid transport element is a continuous, elongated wick 309, and the heater is a resistive heating coil 310 that is in connection with the wick and is positioned at about a midpoint of the wick. The portions of the wick 309 extending beyond the resistive heating coil 310 can be referred to as distal arms of the wick. The electrically conducting terminals 311 of the atomizer 300 are positioned in contact with the wick 309 distal to the resistive heating coil 310. The electrically conducting terminals 311 particularly can be characterized as being in contact with the wick 309 at one or more portions of the wick distal to the resistive heating coil 310. As illustrated, the electrically conducting terminals 311 extend beyond the ends of the wick 309. Such extension is not necessarily required. In light of the nature of the reservoir 244 with its hollow interior portion, an atomizer can be easily positioned interior to the reservoir during assembly of the smoking article. Likewise, as the hollow interior can be shaped and dimensioned to mate with the atomizer, the combination can be easily assembled, and the atomizer can snugly mate with the reservoir while simultaneously placing the wick in fluid connection with the reservoir.

The reservoir can be manufactured from any material capable of being shaped into a rigid or semi-rigid hollow tube while retaining the ability to store a liquid product such as, for example, an aerosol precursor composition, particularly an aerosol precursor fluid. In certain embodiments, the reservoir material can be absorbent, adsorbent, or otherwise porous so as to provide the ability to retain the aerosol precursor composition. As such, the aerosol precursor composition can be characterized as being coated on, adsorbed by, or absorbed in the reservoir material. The reservoir can be positioned within the smoking article to be in substantial contact with one or more transport elements (e.g., wicks). More particularly, a reservoir can be manufactured from any material suitable for retaining the aerosol precursor composition (e.g., through absorption, adsorption, or the like) and allowing wicking away of the precursor composition for transport to the resistive heating element.

The reservoir material is suitable for forming and maintaining an appropriate conformation, such as a substantially tubular shape, and for accommodating therein the suitable components of the smoking article. The reservoir material can be heat resistant so as to retain its structural integrity—e.g., does not degrade—at least at a temperature that is received in a position proximal to the heating temperature provided by the resistive heating element. The size and strength of the reservoir may vary according to the features and requirements of the corresponding electronic smoking article. In particular embodiments, the reservoir can be manufactured from a material suitable for a high-speed, automated manufacturing process. In certain embodiments, the reservoir can comprise a woven or non-woven fibrous mat, which may be rolled or otherwise formed into a tube or hollow cylinder shape. In other embodiments, the reservoir can be a molded tube or hollow cylinder.

According to one embodiment, the reservoir can be manufactured from a cellulose acetate tow which can be processed to form a hollow acetate tube. Cellulose acetate tow can be prepared according to various processes known to one skilled in the art. See, for example, the processes forth in U.S. Pat. No. 4,439,605 to Yabune, U.S. Pat. No. 5,167,764 to Nielsen et al., and U.S. Pat. No. 6,803,458 to Ozaki which are incorporated herein by reference in their entireties. Typically, cellulose acetate is derived from cellulose by reacting purified cellulose from wood pulp with acetic acid and acetic anhydride in the presence of sulfuric acid. The resulting product is then put through a controlled, partial hydrolysis to remove the sulfate and a sufficient number of acetate groups to produce the required properties for a cellulose acetate that is capable of ultimately forming a rigid or semi-rigid hollow tube. Cellulose acetate can then be extruded, spun, and arranged into a tow. The cellulose acetate fibers can be opened, crimped, or a continuous filament.

In further embodiments, the cellulose acetate can be any acetate material of the type that can be employed for providing a tobacco smoke filter for cigarettes. Preferably a traditional cigarette filter material is used, such as cellulose acetate tow or gathered cellulose acetate web. Examples of materials that can be used as an alternative to cellulose acetate include polypropylene tow, gathered paper, strands of reconstituted tobacco, or the like. One filter material that can provide a suitable filter rod and thus a suitable hollow tube reservoir is cellulose acetate tow having 3 denier per filament and 40,000 total denier. As another example, cellulose acetate tow having 3 denier per filament and 35,000 total denier can be used. As another example, cellulose acetate tow having 8 denier per filament and 40,000 total denier can be used. For further examples, see the types of filter materials set forth in U.S. Pat. No. 3,424,172 to Neurath; U.S. Pat. No. 4,811,745 to Cohen et al.; U.S. Pat. No. 4,925,602 to Hill et al.; U.S. Pat. No. 5,225,277 to Takegawa et al. and U.S. Pat. No. 5,271,419 to Arzonico et al.; each of which is incorporated herein by reference.

Cellulose acetate fibers can be mixed with other materials, such as, cellulose, viscose, cotton, cellulose acetate-butyrate, cellulose propionate, polyester—e.g., polyethylene terephthalate (PET), polylactic acid (PLA), activated carbon, glass fibers, metal fibers, wood fibers, and the like. The fibers of a cellulose acetate tow emerging from the spinneret can be bunched together to form a "raw tow" which can be collected into a bale for subsequent processing into a tube as described herein. Additional examples of fiber materials that can be suitable for use in a reservoir according to the present disclosure are described in US Pat Publication No. 2013/0025610 to Sebastian et al., the disclosure of which is incorporated herein by reference.

Cellulose acetate can be processed and formed into a tube using conventional filter tow processing means. For example, a steam bonding process can be used to produce the hollow acetate tubes. Exemplary processes for forming tubes of cellulose acetate can be found US Pat. Publication No. 2012/0255569 to Beard et al. In further embodiments, cellulose acetate can be processed using a conventional filter tow processing unit. For example, filter tow can be bloomed using bussel jet methodologies or threaded roll methodologies. An exemplary tow processing unit has been commercially available as E-60 supplied by Arjay Equipment Corp., Winston-Salem, N.C. Other exemplary tow processing units have been commercially available as AF-2, AF-3 and AF-4 from Hauni-Werke Korber & Co. KG, and as Candor-ITM Tow Processor from International Tobacco Machinery. Other types of commercially available tow processing equipment, as are known to those of ordinary skill in the art, can be employed. Alternative materials for forming the hollow tube reservoir, such as gathered paper, nonwoven polypropylene web, or gathered strands of shredded web, can be provided using the types of materials, equipment and techniques set forth in U.S. Pat. No. 4,807,809 to Pryor et al. and U.S. Pat. No. 5,025,814 to Raker. In addition, representative manners and methods for operating a filter material supply units and filter-making units are set forth in U.S. Pat. No. 4,281,671 to Bynre; U.S. Pat. No. 4,850,301 to Green, Jr. et al.; U.S. Pat. No. 4,862,905 to Green, Jr. et al.; U.S. Pat. No. 5,060,664 to Siems et al.; U.S. Pat. No. 5,387,285 to Rivers and U.S. Pat. No. 7,074,170 to Lanier, Jr. et al.

The hollow acetate tubes as described herein can be particularly useful because of a surprisingly efficient liquid storing capacity. According to one embodiment, the cellulose acetate tow can have a linear mass density of about 0.5 denier per filament (dpf) or greater, about 1 dpf or greater, or about 2 dpf or greater. In other embodiments, the cellulose acetate tow can have a linear mass density of about 0.5 dpf to about 20 dpf, about 0.75 dpf to about 15 dpf, about 1 dpf to about 10 dpf, or about 2 dpf to about 6 dpf. The cellulose acetate used according to the present disclosure can comprise staple fibers. The staple fibers can have an average length of about 0.1 in. to about 6 in., about 0.2 in. to about 5 in. or about 0.25 in. to about 3 in.

The reservoir comprising cellulose acetate can be formed of various compositions and in various manners. In particular embodiments, the reservoir can comprise cellulose acetate fibers. If desired, the reservoir can comprise a binder. Fillers (e.g., cellulose) and fibers formed of different materials also can be used. The reservoir can comprise about 70% to about 99% by weight cellulose acetate fibers, and the weights noted herein are measured on a dry weight basis (i.e., without any aerosol precursor or other fluid therein). More specifically, the reservoir can comprise about 75% to about 98%, about 80% to about 97.5%, or about 90% to about 97% by weight cellulose acetate fibers. The reservoir can comprise about 1% to about 30% by weight of the binder. More specifically, the reservoir can comprise about 2% to about 25%, about 2.5% to about 20%, or about 3% to about 10% by weight of the binder. In specific embodiments, a reservoir according to the disclosure can comprise about 95% to about 97% by weight cellulose acetate fiber and about 3% to about 5% by weight binder. In other specific embodiments, a reservoir according to the disclosure can comprise about 80% to about 85% by weight cellulose acetate fiber and about 15% to about 20% by weight binder. A binder is understood to be a material that imparts a cohesive effect to the fibers used in forming the disclosed reservoirs. For example, the binder can be a material that partially solubilizes the cellulose acetate fibers such that the fibers bind to each other or to further fibrous materials included in the woven or non-woven reservoir. Exemplary binders that can be used include polyvinyl acetate (PVA) binders, starch, and triacetin. One of skill in the art of cigarette filter manufacture may recognize triacetin as being a plasticizer for such filters. As such, it is understood that there may be overlap between the group of binders useful according to the present disclosure and materials that may be recognized in further arts as plasticizers. Accordingly, the cohesion agent used and described herein as a binder may encompass materials that may be recognized in other fields as being plasticizers. Moreover, materials recognized in the field of cigarette filters as plasticizers for cellulose acetate may be encompassed by the use of the term binders herein.

The cellulose acetate fibers can have various cross-sectional shapes—e.g., round, elongated, or multi-lobal. In specific embodiments, cellulose acetate having a tri-lobal or Y-shaped cross-sectional shape can be used.

In some embodiments, a non-woven fibrous mat reservoir according to the present disclosure can be formed by a wet-laid process or by a dry-laid process. When using a wet-laid process, it can be beneficial to use cellulose acetate fibers having shorter lengths—e.g., in the range of about 0.25 in. to about 2 in. When using a dry-laid process, it can be beneficial to use cellulose acetate fibers having longer lengths—e.g., in the range of about 2.5 in. to about 3 in. In each case, a resulting mat comprising the cellulose acetate fibers can be at a thickness of about 1 mm to about 4 mm, about 1.25 mm to about 3.5 mm, or about 1.5 mm to about 3 mm. The cellulose acetate mat can be sized to a desired width. In various embodiments, the width can be about 10 mm to about 25 mm, about 15 mm to about 24 mm, or about 20 mm to about 23 mm. The cellulose acetate mats can be cut to lengths suitable to be rolled into a tube having an outer diameter suitable for insertion into a smoking article as described herein and having an inner diameter suitable to allow insertion of an atomizer therein according to the present disclosure. The ends of the rolled mats can form a butt joint or may overlap. In further embodiments, the cellulose acetate composition can be molded into a formed shape that is substantially tubular. The shaped hollow acetate tube can have one or more shapes formed into the inner wall thereof, such as the diametrically opposed grooves discussed above.

In some embodiments, the fibers of the formed mats can be entangled. For example, hydroentangling and needle punching each can be used separately or in combination. In specific embodiments, needle punching can be used with at least 250, at least 500, at least 1,000, or at least 1,500 needle punches per square inch (NPPSI). In particular, about 250 to about 2,500, about 500 to about 2,000, or about 750 to about 1,500 NPPSI can be used.

According to one embodiment, the reservoir can comprise a mixture of different types of fibers. Suitable fibers for forming such mixture include, but are not limited to, fibers formed from cellulose acetate, wood pulp, wool, silk, polyesters (e.g., polyethylene terephthalate) polyamides (e.g., nylons), polyolefins, polyvinyl alcohol, and the like.

It has been found according to the present disclosure that hydrophilic fibers, particularly cellulose acetate, can be particularly useful in forming a reservoir for an aerosol precursor composition, particularly a composition formed predominately with a polyhydric alcohol, such as glycerin. Such reservoirs can provide improved storage and release of the aerosol precursor composition. For example, such reservoirs can provide for faster loading of the aerosol precursor composition, for more consistent release of the aerosol precursor composition when drawn away, such as by a wick, during use of the smoking article, and a reduction in the total volume of aerosol precursor composition that must be loaded in the reservoir.

In various embodiments, the improved moisture control afforded by electronic smoking articles according to the present disclosure can arise from the nature of the device and its construction, materials used in the construction, and methods of constructing the device. For example, it has been found that a reservoir comprising a woven or nonwoven fabric can provide improved retention of fluid absorbed therein or adsorbed thereon when the fabric is provided in a defined weight bases. In non-limiting embodiments, a woven or nonwoven fabric useful in a reservoir according to the present disclosure can have a basis weight of about 120 grams per square meter (gsm) or greater, about 125 gsm or greater, or about 130 gsm or greater. In further embodiments, the woven or nonwoven fabric can have a basis weight of about 120 gsm to about 220 gsm, about 125 gsm to about 200 gsm, or about 130 gsm to about 180 gsm.

It has been found that a reservoir for use in an electronic smoking article can suffer from its inherent absorptive or adsorptive properties in that water vapor may be taken up from surrounding air, particularly during storage, and thus dilute the aerosol precursor composition already provided therein. In some instances, the amount of water vapor captured by the reservoir can exceed its holding capacity, and "sweating" can occur wherein liquid releases from the reservoir into the interior of the housing forming the smoking article. This movement of liquid through the device can have deleterious effects in relation to corrosion and possible interference or other interaction with electrical components of the device. Moreover, depending upon the nature of the housing, liquid released by the reservoir may move out of the housing, which may be unfavorable to a consumer.

A common consideration for a reservoir in an electronic smoking article is the ability of the reservoir to hold a sufficient volume of aerosol precursor composition to form the desired amount of aerosol. In light of the relatively small size of many electronic smoking articles, it is typically desirable to limit the size of components, including the reservoir, to only the absolutely necessary maximum dimensions (e.g., length and diameter). It has been recognized according to the present disclosure, however, that utilization of a high basis weight woven or nonwoven fabric in the reservoir of an electronic smoking article can be effective to prevent or reduce loss of aerosol precursor liquid from the reservoir into the open housing of the device. The increased basis weight can provide a greater holding capacity without the need to significantly increase the absolute dimensions (e.g., the length and diameter) of the reservoir.

In addition or in the alternate to increased basis weight, the ability of the reservoir to retain the aerosol precursor composition in liquid form can be improved through surface treatment of the reservoir. For example, one or more surfaces of the reservoir can be treated to reduce or prevent passage of liquid therethrough. For example, a hydrophobic material can be used. The liquid transport element can thus provide the only or main conduit for passage of any liquid out of the reservoir.

In other embodiments, sweating of a reservoir may be reduced or eliminated by limiting the total amount of aerosol precursor composition that is applied to the woven or nonwoven fabric. In particular, the article may be limited such that the weight of aerosol precursor fluid that is stored in the reservoir does not exceed a defined weight relative to the saturation capacity of the reservoir. An absorptive or adsorptive reservoir can exhibit a saturation capacity, which can be defined as the mass of a liquid that may be retained by a reservoir of a defined composition and mass above which the reservoir can no longer absorb or adsorb any further amount of the liquid.

A material useful as a reservoir according to the present disclosure can have a saturation capacity of up to about 2,000%, up to about 1,900%, or up to about 1,800% by weight relative to an aerosol precursor composition useful according to the present disclosure. In further embodiments, a reservoir can have a saturation capacity of about 800% to about 2,000%, about 900% to about 1,800%, about 1,000% to about 1,700%, or about 1,200% to about 1,600% by weight.

In some embodiments, the weight of aerosol precursor fluid in the reservoir relative to the saturation capacity of the reservoir is no greater than about 80%. For example, a fabric reservoir having a weight of 5 g and a saturation capacity of about 1,500% by weight relative to an aerosol precursor composition can hold a maximum of about 75 g of the aerosol precursor composition. Such reservoir loaded with no greater than about 80% of the saturation capacity would be loaded with no greater than about 48 g of the aerosol precursor composition. In further embodiments, the weight of aerosol precursor fluid in the reservoir relative to the saturation capacity of the reservoir is no greater than about 60%. By thus limiting the weight of aerosol precursor fluid originally loaded into the reservoir, the amount of water vapor that may be taken up during storage may be insufficient to load the reservoir sufficiently near or beyond its saturation capacity and cause sweating or similar release of fluid from the reservoir.

The filaments used in a wick according to the present disclosure can be formed of any material that provides sufficient wicking action to transport one or more components of the aerosol precursor composition along the length of the filament. Non-limiting examples include natural and synthetic fibers, such as cotton, cellulose, polyesters, polyamides, polylactic acids, glass fibers, combinations thereof, and the like. Other exemplary materials that can be used in wicks include metals, ceramics, and carbonized filaments (e.g., a material formed of a carbonaceous material that has undergone calcining to drive off non-carbon components of the material). Exemplary materials that may be used as a wick according to the present disclosure are described in U.S. patent application Ser. No. 13/802,950, filed Mar. 13, 2013, the disclosure of which is incorporated herein by reference in its entirety.

In particular embodiments, a wick useful as the liquid transport component is a braided wick. The braided wick can be formed from at least 3 separate fibers or yarns. Further, the braided wick can be formed from at least 4, at least 6, at least 8, at least 10, at least 12, at least 14, or at least 16 separate fibers or yarns. Each of the separate fibers or yarns may be identical in composition. Alternatively, the separate fibers or yarns may comprise fibers or yarns formed of two or more different compositions (e.g., a fiberglass yarn braided with a cotton yarn). Thus, the braided wick can be formed of a plurality of synthetic fibers or yarns, a plurality of natural fibers or yarns, of a combination of at least one synthetic fiber or yarn and at least one natural fiber or yarn. In certain embodiments, E-glass can be used. In some embodiments, C-glass can be used.

A braided wick in particular may be provided as a component of a sheath/core yarn. In particular, a first wick material can form a yarn core, and a second wick material can surround the core to form a yarn sheath. The sheath and core can differ in at least one of physical structure and the material from which the yarn is formed. In a preferred example, a twisted yarn can comprise the core, and braided yarn can form the sheath.

Devices according to the present disclosure can include even further elements useful in controlling moisture. In some embodiments, one or more mechanical elements can be included in an electronic smoking article, such as a cartridge thereof, and can be adapted to prevent fluid passage across a barrier. For example, in some embodiments, an electronic smoking article according to the present disclosure can comprise a housing having an air inlet adapted for entry of air into the housing and an air outlet adapted for exit of a formed aerosol, the inlet and the outlet having an air passage therebetween. The smoking article further can comprise a reservoir within the housing that is configured to hold an aerosol precursor fluid and a heater in fluid communication with the reservoir. Still further, the smoking article can include one or more valves adapted to prevent fluid passage across a barrier. For example, a first check valve can be positioned at the air inlet and a second check valve can be positioned at the air outlet.

One embodiment of a cartridge 404 according to the present disclosure is shown in FIG. 4. As seen therein, the cartridge 404 comprises a housing 403 with a housing receptacle 440 at a first end thereof that is adapted to interconnect with a control body projection (see element 224 in FIG. 2, for example). One or more cut-outs may be formed in the housing 403 at the first end thereof to form an air inlet 418. A plurality of air inlets 418 (one to five, for example) may be included. At least one air outlet 428 can be provided at a second, opposing end of the housing 403. As illustrated, the housing 403 further includes a reservoir 444, which may have a construction as otherwise disclosed herein. The reservoir in some embodiments can be substantially cylindrical. As seen in FIG. 4, an air passage 480 interconnects the air inlet 418 and the air outlet 428 and passes through the interior opening of the cylindrical reservoir 444. The cartridge 404 also can include a first end wall 460 formed adjacent the housing receptacle 440 and forming a terminal base thereof. Formed in the first end wall 460 is a first check valve 465. A second end wall 470 is included near the second end of the housing 403. Formed in the second end wall 470 is a second check valve 475. In the first check valve 465 and second check valve 475 as illustrated, a simple flap valve is shown in an open position indicating air flow passing through the device. A variety of valves, however, may be utilized, such as ball valves and heart valves.

The first end wall 460 and second end wall 470 can form a chamber 490 that can be adapted to retain all liquids (e.g., aerosol precursor composition or ambient water vapor entrained during manufacturing) therein. The first check valve 465 and second check valve 475 in particular can be adapted to form a seal that is substantially liquid impermeable (particularly water and vapor) when in the closed position. As such, any sweating or other loss of liquid from the reservoir 444 may be retained completely within the chamber 490 so as to disallow any leakage through the first end (e.g., the housing receptacle 440) or second end (e.g., the mouth end 430) of the housing 403.

The first check valve and the second check valve may be adapted to open only in the direction of air flow from the air inlet to the air outlet (the air flow being illustrated by the dashed arrows in FIG. 4). As such, in some embodiments, one or both of the first check valve and the second check valve can be one way check valves. In further embodiments, one or both of the first check valve and the second check valve can be two way check valves, if desired. Any check valve suitably sized for inclusion in a device as described herein may be used.

As illustrated in FIG. 4, a cartridge 404 also may include an atomizer formed of a transport element 436 adapted to wick or otherwise transport an aerosol precursor composition stored in the reservoir 444 to a heater 434 that heats and vaporizes the aerosol precursor composition and form an aerosol when mixed with the air flowing through the air passage 480. In some embodiments, the heater can be positioned at least partially within the air passage.

Separately or in combination with the inclusion of check valves as illustrated in FIG. 4, a smoking article according to the present disclosure may include an absorptive material. Preferably, the absorptive material is adapted for absorbing any free liquid within the housing 403 without substantially withdrawing any of the aerosol precursor composition from the reservoir 444. The absorptive material, for example, may be a fibrous material formed of natural and/or synthetic fibers. Porous ceramics and the like also may be used. In particular, the absorptive material can be provided as a lining on all or part an interior wall of the housing 403. In some embodiments, as illustrated in FIG. 4, the absorptive material may be located only at one or both of the first end and the second end of the housing 403. In FIG. 4, the absorptive material 495 is located at the respective ends but interior to the first end wall 460 and the second end wall 470—i.e., within the chamber 490.

The present disclosure further provides methods of making electronic smoking articles. In some embodiments, the method can comprise providing a reservoir, which can comprise a woven or nonwoven fabric and which may be provided in the form of a cylinder having a hollow interior portion. At least part of the hollow interior can be shaped and dimensioned to accommodate one or more further components of the smoking article. The method can further include the step of inserting an atomizer into the hollow interior of the reservoir. The atomizer can comprise a liquid transport element, a heater, and electrical contacts. The method can further include the steps of inserting the cylinder and atomizer into a hollow shell, and connecting the atomizer to a power source. The power source can be a battery. Portions of the liquid transport element can be attached to or embedded in the reservoir to form a fluid connection that enables transport of the aerosol precursor composition out of the reservoir. The atomizer can comprise a continuous, elongated wick having two opposing ends. The wick particularly can be a braided wick and/or can comprise C-glass. The atomizer can further comprise a heater in connection with the wick and positioned at about a midpoint thereof. The atomizer also can comprise electrically conducting terminals positioned in physical contact with the wick and in electrical contact with the heater which, in some embodiments, can be a resistive heating element.

The methods of preparing electronic smoking articles according to the present disclosure can be adapted to improve moisture control. In particular, the methods can be adapted to prevent or reduce the absorption or adsorption of water vapor (or other vapors) from the air by the reservoir. Such methods can thus ensure that the aerosol formed during use of the smoking article is substantially identical in composition to the aerosol precursor composition applied to the reservoir during processing. In particular, it can substantially prevent dilution of the formed aerosol with excess water absorbed or adsorbed by the reservoir during processing, including manufacturing and shipping.

In some embodiments methods according to the present disclosure can comprise providing a reservoir as described herein. The reservoir specifically can be configured to hold an aerosol precursor fluid, and the reservoir can comprise a woven or nonwoven fabric. The method further can comprise inserting the reservoir into a hollow housing, and adding the aerosol precursor fluid to the reservoir. The aerosol precursor composition can be added to the reservoir one or both of before or after inserting the reservoir into the hollow housing. The housing may be a cartridge housing (which may be separate from a control body housing). Alternatively, the housing may be a single housing that encloses both the reservoir and one or both of a power source and a control component. Preferably, the assembly steps described herein can be carried out under an ambient relative humidity that is maintained below a defined percentage. For example, the assembly can be carried out under an ambient relative humidity of no greater than about 40%, no greater than about 35%, no greater than about 30%, or no greater than about 20%.

In some embodiments, assembly of an electronic smoking article or a component thereof (specifically a cartridge component that includes a reservoir) can be carried out under conditions adapted to substantially prevent absorption or adsorption of any water vapor during assembly. Substantially preventing absorption or adsorption can indicate that the reservoir absorbs or adsorbs less than 1% by weight, preferably less than 0.5% by weight, of water from the ambient atmosphere relative to the dry weight of the reservoir. Conditions adapted to substantially prevent absorption or adsorption of any water vapor during assembly can include carrying out the assembly under an inert atmosphere. As a non-limiting example, the inert atmosphere can be an argon atmosphere (or similar gas, such as a further noble gas).

In further embodiments, moisture control can be provided in relation to certain steps of the assembly of the device. For example, in some embodiments, assembly of a device according to the present disclosure can include engaging an open end of a hollow housing with a cap element or like end piece. The method particularly can be adapted to provide specific crimping of the housing end to the cap, the crimping being adapted to form a non-hermetic seal that allows for gas transfer around the seal but that prevents passage of liquid, particularly hydrophilic liquids, around the seal. Such crimping can be particularly useful in preventing leakage of any free liquid out of a housing of an electronic smoking article.

In some embodiments, moisture control can be provided in relation to packaging of an electronic smoking article or a component thereof. Such packaging methods may relate specifically to any component of an electronic smoking article comprising a reservoir adapted for storing an aerosol precursor composition. For example, the packaging methods may particularly relate to packaging of a cartridge of an electronic smoking article—e.g., a housing including a reservoir and being adapted to releasably engage a control body and/or power source.

In a non-limiting example, a packaging method according to the present disclosure can comprise providing a cartridge (or other electronic smoking article or component thereof)

with a reservoir therein. The reservoir specifically can comprise a woven or nonwoven fabric and can have an aerosol precursor fluid therein. The method further can comprise positioning the cartridge within a non-hermetically sealed display package. The display package particularly may be formed of a material that is substantially impermeable to water vapor, such as a polymeric material (e.g., a thermoplastic material), for example a polycarbonate, a polyester, or the like. The non-hermetically sealed display package can be a package that is adapted to store the smoking article in a manner that is visible from outside of the package. The package may be non-hermetically sealed in that the package comprises at least two pieces that releasably engage one another, and the engagement is adapted to allow limited gas transfer but substantially prevent passage of liquids (particularly water) therethrough.

The packaging methods further can include additional steps that are adapted to provide for moisture control. For example, in some embodiments, the methods further may comprise covering any opening in the non-hermetically sealed display package with a water-tight sealing tape. In particular, the water-tight sealing tape can be adapted to prevent transfer of water in a liquid or vapor form. The sealing tape can be applied, for example over the joint formed by the engagement of the two pieces forming the display package. An exemplary display case that may be utilized in a method as described herein is described in U.S. patent application Ser. No. 29/447,898, filed Mar. 7, 2013, the disclosure of which is incorporated herein by reference in its entirety.

In a further example, packaging methods may comprise including an insert in the non-hermetically sealed display package. The insert may include a material adapted to control moisture within the package. For example, a desiccant may be included in the insert so as to preferentially absorb water vapor and substantially prevent absorption or adsorption of water vapor by the reservoir of the electronic smoking article. In another non-limiting example the insert may comprise a humidity control device that is adapted to maintain a relative humidity within the package that is within a desired range. Examples of humidity control devices include those commercially available under the tradenames HUMIDIPAK® or BOVEDA®. In some embodiments, the humidity control device may be adapted to maintain a relative humidity within the package of about 5% to about 50%, about 10% to about 45%, or about 15% to about 40%.

In yet a further example, packaging methods may comprise providing a double barrier package. Specifically, the electronic smoking article may be enclosed by a polymeric barrier within the non-hermetically sealed display package. For example, a polymeric barrier, such as a vapor-impermeable film, may line the interior of the non-hermetically sealed display package. Alternatively, the electronic smoking article may be wrapped or otherwise sealed within a polymeric bag and placed inside the non-hermetically sealed display package. Still further, the electronic smoking article may be encased by a blister package and placed inside the non-hermetically sealed display package. Examples of blister packs and related packaging may be found in the following: U.S. Pat. No. 3,610,410 to Seeley; U.S. Pat. No. 3,689,458 to Hellstrom; U.S. Pat. No. 3,732,663 to Geldmacher et al.; U.S. Pat. No. 3,792,181 to Mahaffy et al.; U.S. Pat. No. 3,812,963 to Zahuranec et al.; U.S. Pat. No. 3,948,394 to Hellstrom; U.S. Pat. No. 3,967,730 to Driscoll et al.; U.S. Pat. No. 4,120,400 to Kotyuk; U.S. Pat. No. 4,169,531 to Wood; U.S. Pat. No. 4,383,607 to Lordahl et al.; U.S. Pat. No. 4,535,890 to Artusi; U.S. Pat. No. 5,009,894 to Hsiao; U.S. Pat. No. 5,033,616 to Wyser; U.S. Pat. No. 5,147,035 to Hartman; U.S. Pat. No. 5,154,293 to Gould; U.S. Pat. No. 5,878,887 to Parker et al.; and U.S. Pat. No. 6,520,329 to Fuchs et al., each of which is incorporated herein by reference.

Any of the foregoing embodiments may be combined with other methods and materials useful for reducing or preventing undesired liquid passage in an electronic cigarette. For example, U.S. Pat. App. Pub. Nos. 2013/0306064 and 2013/0306065 to Thorens et al. disclose a leakage preventer, and the disclosures of these documents are incorporated herein by reference in their entireties.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A method of assembling an electronic smoking article, the method comprising:
   providing a reservoir that is configured to hold an aerosol precursor fluid, the reservoir comprising a woven or nonwoven fabric;
   inserting the reservoir into a hollow housing; and
   adding the aerosol precursor fluid to the reservoir before or after said inserting; wherein the method of assembling carried out under an ambient relative humidity of no greater than about 40%, wherein the reservoir has a saturation capacity; and wherein the aerosol precursor fluid is added in an amount such that the weight of aerosol precursor fluid held by the reservoir relative to the saturation capacity of the reservoir is no greater than about 80%.

2. The method of claim 1, wherein the method of assembling is carried out under an inert atmosphere.

3. The method of claim 2, wherein the inert atmosphere is an argon atmosphere.

4. The method of claim 1, wherein the woven or nonwoven fabric has a basis weight of about 120 gsm or greater.

5. The method of claim 1, wherein the nonwoven fabric comprises cellulose acetate.

6. The method of claim 1, wherein the reservoir saturation capacity is about 800% to about 2,000% by weight relative to the aerosol precursor fluid.

* * * * *